(12) United States Patent
Chakravarty et al.

(10) Patent No.: US 7,119,199 B2
(45) Date of Patent: Oct. 10, 2006

(54) PROCESS FOR THE PREPARATION OF PYRIDOPYRIMIDONES

(75) Inventors: Sarvajit Chakravarty, Mountain View, CA (US); Sundeep Dugar, San Jose, CA (US); Richland Tester, Alameda, CA (US); Aurelia Conte, Loerrach (DE)

(73) Assignee: Scios INC, Fremont, CA (US)

( * ) Notice: Subject to any disclaimer, the term of this patent is extended or adjusted under 35 U.S.C. 154(b) by 0 days.

(21) Appl. No.: 11/029,139

(22) Filed: Dec. 31, 2004

(65) Prior Publication Data

US 2005/0176957 A1    Aug. 11, 2005

Related U.S. Application Data

(60) Provisional application No. 60/534,057, filed on Dec. 31, 2004.

(51) Int. Cl.
*C07D 239/91* (2006.01)
*C07D 471/04* (2006.01)

(52) U.S. Cl. ........................ 544/279; 544/287; 544/289
(58) Field of Classification Search ................ 544/279, 544/287, 289
See application file for complete search history.

(56) References Cited

OTHER PUBLICATIONS

Brown, D. J. et a, Australian Journal of Chemistry, 1985 vol. 38, No. 3, pp. 467-474.*
Bennett, et al., J. Med. Chem, 1981, 24:382-389.
Ellingboe, et al., J. Med. Chem, 1994, 37:542-550.
Gonzalgo, et al., The Journal of Urology, Aug. 2003, 170:503-506.
LoRusso, et al., Clinical Cancer Research, Jun. 2003, 9:2040-2048.
Tomita et al., J. Med. Chem., 2002, 45:5564-5575.
International Search Report for PCT/US04/44064, mailed Jul. 14, 2005, 2 pgs.
Brown, et al., Australian Journal of Chemistry, 1985, pp. 467-474, vol. 38:3.

* cited by examiner

*Primary Examiner*—Thomas C. McKenzie
(74) *Attorney, Agent, or Firm*—Scios Inc.

(57) ABSTRACT

The present invention is directed to a method for producing a pyridopyrimidone of the formula

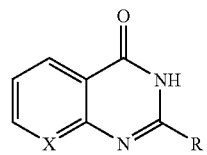

wherein X is N or CH and R is an aryl, heteroaryl or alkyl group, said method comprising the step of reacting an acid derivative of the formula:

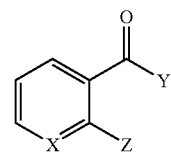

wherein X is N or CH; Y is an appropriate leaving group; Z is a halogen, $OR^1$, $NHR^1$, or $SR^1$; and $R^1$ is a lower alkyl; and the amidine derivative is

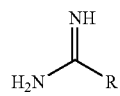

wherein R is an aryl, heteroaryl or alkyl group.

3 Claims, No Drawings

PROCESS FOR THE PREPARATION OF PYRIDOPYRIMIDONES

RELATED APPLICATION

This application claims the benefit of priority of U.S. Provisional Patent Application No. 60/534,057, filed Dec. 31, 2004, hereby incorporated by reference in its entirety.

FIELD OF THE INVENTION

The present invention relates to the preparation of 2 substituted pyridopyrimidones. More particularly, the present invention relates to the preparation of 2 substituted pyridopyrimidones through derivatives of acids and amidines as provided herein.

BACKGROUND

Pyridopyrimidones are versatile pharmacophores in medicinal chemistry. Their heterocyclic structure is found in several biologically active molecules. They also serve as key intermediates for the synthesis of several biologically active molecules, such as pyridoquinazoline inhibitors of receptor tyrosine kinases, CCKA receptor antagonists, anti-bacterial agents, inhibitors of human neutrophil elastase, diuretics, anti-hypertensives, angiotensin II antagonists, and anti-allergics. See for example Pyrido[2,3-d]pyrimidine angiotensin II antagonists. Ellingboe J. W., Antane M., Nguyen T. T., Collini M. D., Antane S., Bender R., Hartupee D., White V., McCallum J., Park C. H., et al. J Med Chem. 1994 Feb. 18; 37(4):542–50; Antihypertensive activity of 6-arylpyrido [2,3-d]pyrimidine-7-amine derivatives. Bennett L. R., Blankley C. J., Fleming R. W., Smith R. D., Tessman D. K. J Med Chem. 1981 April; 24(4):382–9; and Synthesis and structure-activity relationships of novel 7-substituted 1,4-dihydro-4-oxo-1-(2-thiazolyl)-1,8-naphthyridine-3-carboxylic acids as antitumor agents. Part 1. Tomita K, Tsuzuki Y, Shibamori K, Tashima M, Kajikawa F, Sato Y, Kashimoto S, Chiba K, Hino K. J Med Chem. 2002 Dec. 5; 45(25): 5564–75 and. Pyrimidones or molecules derived from pyrimidone cores are found in several active pharmaceutical products. Examples of such pharmaceutical products include Iressa® and Viagra®. See for example Improvements in Quality of Life and Disease-related Symptoms in Phase I Trials of the Selective Oral Epidermal Growth Factor Receptor Tyrosine Kinase Inhibitor ZD1839 in Non-Small Cell Lung Cancer and Other Solid Tumors. LoRusso P. M., Herbst R. S., Rischin D., Ranson M., Calvert H., Raymond E., Kieback D., Kaye S., Gianni L., Harris A., Bjork T., Maddox A. M., Rothenberg M. L., Small E. J., Rubin E. H., Feyereislova A., Heyes A., Averbuch S. D., Ochs J., Baselga J. Clin Cancer Res. 2003 June; 9(6):2040–8 and Clinical Efficacy of sildenafil Citrate and Predictors of Long-term Response. Gonzalgo M. L., Brotzman M., Trock B. J., Geringer A. M., Burnett A. L., Jarow J. P. J Urol. 2003 August; 170 (2):503–506.

While there are various methods for making pyridopyrimidones, they often involve multiple steps and result of various side reactions. An example of one such method for making 2 substituted pyridopyrimidones is illustrated below:

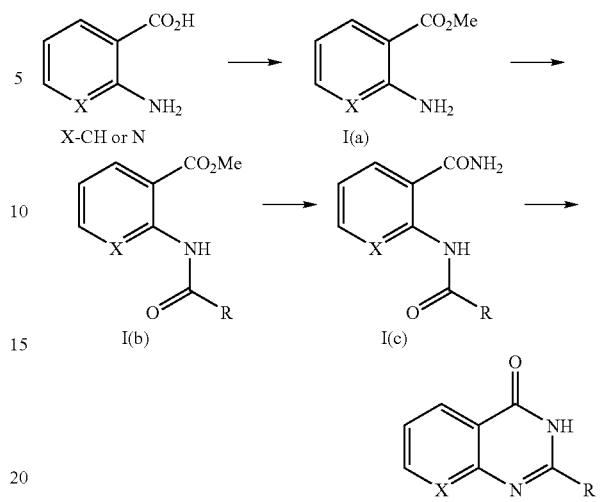

Pursuant to this scheme, the acylation of 2-aminonicotinoate, with an appropriate benzoyl chloride is followed by ammonolysis of the ester. The intermediate bis-amide is then subjected to base promoted cyclization to obtain the desired pyrimidone.

Although this scheme provides a reasonable path to the desired pyrimidones, the conversion of intermediate Ia to intermediate Ib does suffer from bis-acylation as a major side reaction, and the conversion of intermediate Ib to intermediate Ic requires the use of ammonia under pressure.

Given the useful applications for pyridopyrimidones, it is desirable to have a facile route and method for their synthesis, in particular, routes and methods which yield minimal side reactions without unnecessary and sometimes problematic or toxic reagents.

SUMMARY OF THE INVENTION

The present invention is directed to a process for the preparation of a pyridopyrimidone of the formula

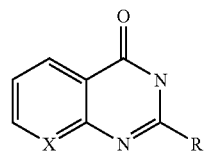

wherein X is N or CH and R is an aryl, heteroaryl or alkyl group. In one embodiment, the process involves reacting an acid derivative of the formula:

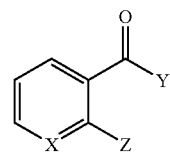

wherein X is N or CH; Y comprises an appropriate leaving group; Z is a halogen, $OR^1$, $NR^1$, or $SR^1$; and $R^1$ is a lower alkyl ($C_1$ to $C_4$) with an amidine derivative of the formula

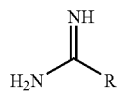

where R is defined as above.

Preferably the Y is $OR^1$, $SR^1$, Cl, F, or

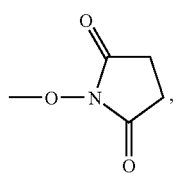

or any other activated ester. By activated ester, it is meant to include any ester that can be characterized as having an increased chemical reactivity due to the presence of an enhanced leaving group. Depending upon available reagents, resources and desired results, one skilled in the art may choose the appropriate activated ester. More preferably, Y is Cl or F.

In a preferred embodiment, the invention is directed to the use of a nicotinic acid derivative with an amidine derivative to yield the desired 2 substituted pyridopyrimidone.

DISCLOSURE OF THE INVENTION

The present invention provides for a facile synthetic route for making 2-substituted pyrimidones. In an exemplary embodiment, the invention is directed to the use of a single step reaction involving derivatives of acids and amidines. Preferably, said acid derivatives comprise derivatives of nicotinic acid and said amidines comprise a benzyl substituent. In a related embodiment, said amidines comprise an acyl substituent. In another preferred embodiment, the nicotinic acid derivative is 2-fluoro-3-nicotonylchloride.

A modified approach is also provided herein whereby the issues of bis-acylation and the need for pressurized ammonia are removed. As outlined below in Schemes IIa and IIb, this approach provides for a shorter synthetic pathway while alleviating other operational issues.

Scheme IIa:

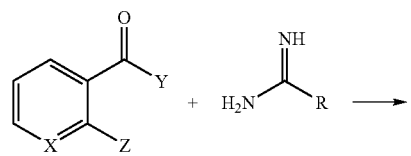

X = N, CH
Y = $OCH_3$, Cl
Z = Cl, F

-continued

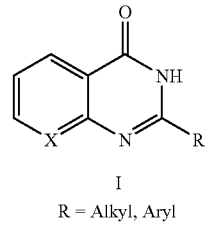

R = Alkyl, Aryl

The synthetic pathway outlined in Scheme IIa can involve two distinct sequences depending upon the substrate used as outlined in Scheme IIb, paths 1 and 2.

Scheme IIb:

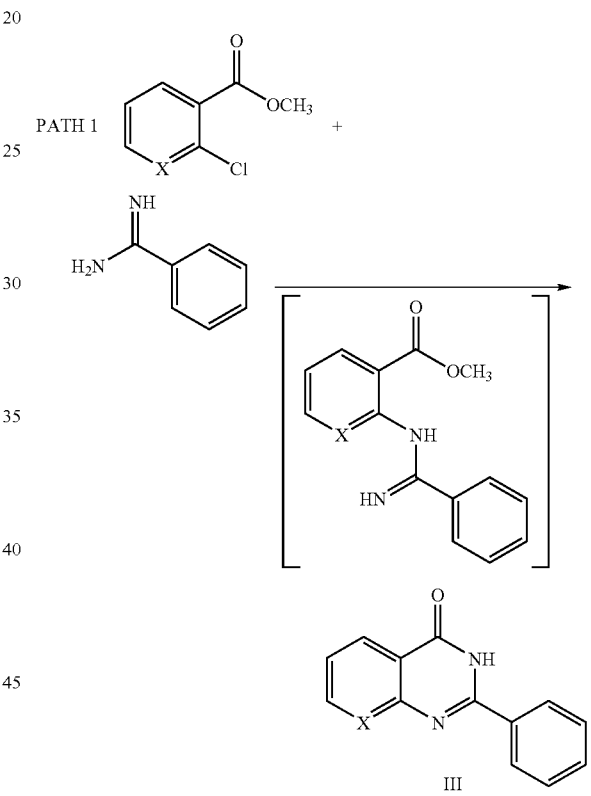

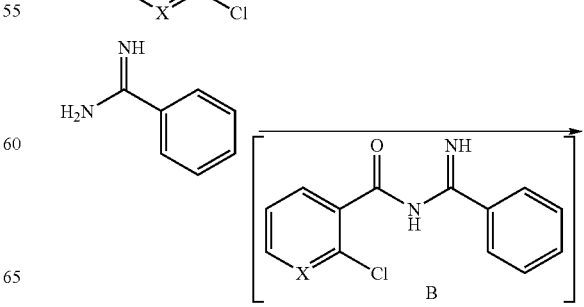

-continued

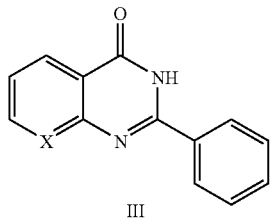

III

EXPERIMENTAL

As observed by comparison of Tables 1 and 2 below, the acid derivative substrate for use in the present invention preferably comprises a pyridine ring. Without being bound to any particular theory, this suggests that intra-molecular cyclization can be optimized through activation of the associated halogen bond. Accordingly, a preferred embodiment of the present invention involves the use of 2-halonicotinic acid derivatives to yield the desired 2 substituted pyrimidones.

According to the approaches set forth in Scheme IIb above, entries 1 and 2 from Table 2 suggest that of the two outlined pathways, path 2 gives better yield. This may be due to the reduced reactivity of the ester thereby allowing for alternate reaction pathways. The primary effect of changing the halogen moiety from chloro to fluoro seems to be on the yield of the product. See entries 2 and 3 in Table 2. As the reaction was monitored for completion it was observed that the acylation of the amidine was rapid in both instances, however, in the case of the 2-chloronicotinoyl chloride the ring closure to give the pyrimidone occurred at a significantly slower rate. This suggests a preferred nicotinoyl substrate for the conversion as being 2-fluoro-3-nicotonyl-chloride.

Additionally, investigation of the amidine variations indicates that though aryl amidines, entries 1–5 and 8, Table 2, are better, the reaction also works with imidates, entries 6 Table 2. This suggests an added versatility to the reaction.

TABLE 1

| Entry | Aroyl substrate | Amidine | Product | Yield |
|---|---|---|---|---|
| 1 | 2-chlorobenzoyl chloride | benzamidine | 2-phenylquinazolin-4(3H)-one | Poor yield |
| 2 | 2-fluorobenzoyl chloride | benzamidine | 2-phenylquinazolin-4(3H)-one | Poor yield |

TABLE 2

| Entry | Aroyl substrate | Amidine | Product | Reaction conditions | Yield |
|---|---|---|---|---|---|
| 1 | methyl 2-chloronicotinate | benzamidine | 2-phenylpyrido[2,3-d]pyrimidin-4(3H)-one | DMF/triethylamine, 90° C. 4 hours | 34% |

TABLE 2-continued

| Entry | Aroyl substrate | Amidine | Product | Reaction conditions | Yield |
|---|---|---|---|---|---|
| 2 | 2-chloro-pyridine-3-carbonyl chloride | benzamidine | 2-phenyl-pyrido[2,3-d]pyrimidin-4(3H)-one | DMF/triethylamine, 90° C. 4 hours | 56% |
| 3 | 2-fluoro-pyridine-3-carbonyl chloride | benzamidine | 2-phenyl-pyrido[2,3-d]pyrimidin-4(3H)-one | DMF/triethylamine, 90° C. 4 hours | 87% |
| 4 | 2-fluoro-pyridine-3-carbonyl chloride | 5-chloro-2-fluoro-benzamidine | 7-fluoro-2-(5-chloro-2-fluorophenyl)-pyrido[2,3-d]pyrimidin-4(3H)-one | Acetonitrile/triethylamine, reflux, 4 hours. | 84% |
| 5 | 2,6-difluoro-pyridine-3-carbonyl chloride | 5-chloro-2-fluoro-benzamidine | 7-fluoro-2-(5-chloro-2-fluorophenyl)-pyrido[2,3-d]pyrimidin-4(3H)-one | Acetonitrile/di-isopropylethylamine, reflux, 4 hours. | 69% |
| 6 | 2-fluoro-pyridine-3-carbonyl chloride | O-methylisourea | 2-methoxy-pyrido[2,3-d]pyrimidin-4(3H)-one | DSMF/triethylamine, 90° C. 4 hours | 51% |
| 7 | 2-fluoro-pyridine-3-carbonyl chloride | acetamidine | 2-methyl-pyrido[2,3-d]pyrimidin-4(3H)-one | DMF/triethylamine, 90° C. 4 hours | 49% |
| 8 | 4-methoxy-2-chloro-pyridine-3-carbonyl chloride | 5-chloro-2-fluoro-benzamidine | 5-methoxy-2-(5-chloro-2-fluorophenyl)-pyrido[2,3-d]pyrimidin-4(3H)-one | DMF/triethylamine, 90° C. 4 hours | 78% |

Note: all yields calculated based on the quantity of the 2-halo nicotinic acid used for the reaction.

EXAMPLE 1

Synthesis of 2-(2-fluoro,5-chloro)phenyl-7-fluoro-pyrido-8-pyrimidone. (Entry 7, Table II)

2,6 difluoronicotinic acid, (0.479 g, 3.012 mmol) was suspended in 30 mL dry methylene chloride and treated with thionyl chloride (2.5 mL, 34.27 mmol), under reflux for 90 minutes. The reaction mixture was cooled to room temperature and the solvents removed under reduced pressure on a rotary evaporator, the residue obtained was further dried under high vacuum to give 2,6 difluoronicotinoyl chloride. 2,6 difluoronicotinoyl chloride was suspended in 30 mL acetonitrile, to this was added 2-fluoro-5-chlorobenzamidine (0.52 g, 3.012 mmol) and di-isopropylehylamine (1.04 mL, 6/024 mmol). The reaction mixture was allowed to stir at room temperature for one hour, at this time the formation of the acyl amidine intermediate was confirmed by LCMS as set forth below. The reaction mixture was then heated to reflux for three hours and cooled to room temperature. The reaction mixture was concentrated to dryness on a rotary evaporator and the residue was taken up in water. The suspension obtained was placed in an ice bath and acidified with 10% aq. hydrochloric acid to pH 4. The solid precipitate that formed was filtered and washed with water and anhydrous ether and dried to give 0.611 g of 2-(2-fluoro, 5-chloro) phenyl-7-fluoro-pyrido-8-pyrimidone. ESIMS $M^+_{obsd.}$ 294.3 $M^+_{cald.}$ 293.66. $^1$H NMR $d_6$ DMSO. δ13.15, bs, 1H; δ8.7, t, 1H; δ7.9, m, 1H; δ7.75, m, 1H; δ7.5, t, 1H; δ7.4, dd, 1H;

LCMS—(HPLC conditions): Column: $C_{18}$ Phenomenex, 30 mm length, 4.6 mm, I.D., 5 micron. Flow rate: 2 mL/min. Diode array detection. 5%–95% acetonitrile; (0.1% TFA)/Water, (0.1% TFA) in 5 minutes.

EXAMPLE 2

Synthesis of 2-(5-Chloro-2-fluoro-phenyl)-7-fluoro-3H-pyrido[2,3-d]pyrimidine-4-one (Entry 5, Table II)

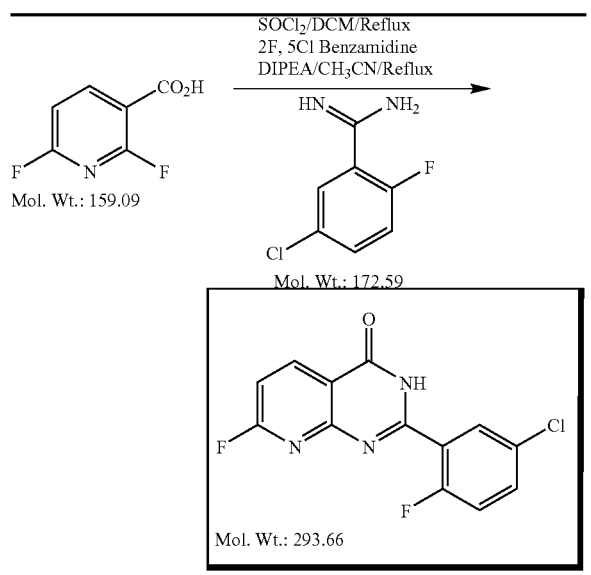

| Reagent | FW | d | Amount Used | mmol | Ratio |
|---|---|---|---|---|---|
| 2,6 di-fluoro-3-pyridine carboxylic acid | 159.09 | | 1.03 g | 6.47 | 1 |
| Thionyl chloride | 118.97 | 1.631 | 4.70 mL | 64.7 | 10 |

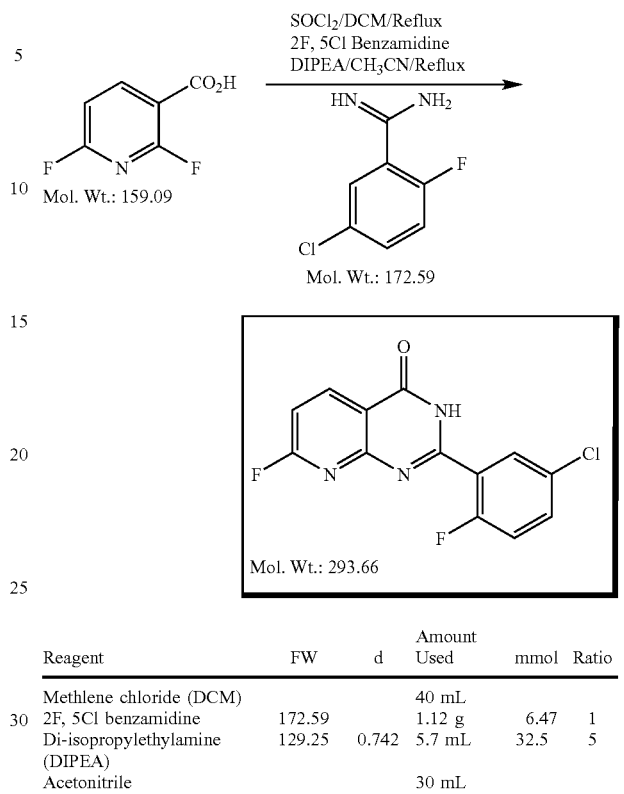

| Reagent | FW | d | Amount Used | mmol | Ratio |
|---|---|---|---|---|---|
| Methylene chloride (DCM) | | | 40 mL | | |
| 2F, 5Cl benzamidine | 172.59 | | 1.12 g | 6.47 | 1 |
| Di-isopropylethylamine (DIPEA) | 129.25 | 0.742 | 5.7 mL | 32.5 | 5 |
| Acetonitrile | | | 30 mL | | |

The acid was suspended in 40 mL DCM and brought to reflux. During reflux a clear solution was obtained. After 3 hours the reaction mixture was cooled to room temperature and the reaction mixture concentrated on a rotary evaporator. The residue was dried on a vacuum pump for 30 minutes. To this dry residue was added 30 mL acetonitrile, the amidine and DIPEA. The mixture was brought to reflux under nitrogen and maintained at reflux for 70 minutes. Analysis of the reaction mixture at this time (LCMS), showed one major peak, mass 294. The reaction mixture was cooled to room temperature and concentrated on a rotary evaporator to give a dry residue. 30 mL of methanol was added to this residue and a precipitate formed. The solid was filtered and washed with ether and dried under vacuum to give a solid, 0.8 g. This material was dissolved in DMF to obtain a clear solution and analyzed by LCMS. One major peak, mass 294.

The filtrate was concentrated to a solid and then suspended in 50 mL water. A precipitate forms. This suspension was acidified to pH 1–2, with 10% HCl. The solid that separates was filtered and washed with ether and dried under high vacuum. The analysis of this product shows it to be identical to the solid obtained from the first crop. (2) 0.58 g of solid was obtained in this fashion. Both batches of solid were combined and used for further reactions. 1.38 g total yield. Approximate yield 70%.

The present invention provides a facile process for making 2-substituted pyridopyrimidones. The process can be used for entry into several pharmacophores of significant interest to medicinal chemists. Furthermore, this process enables one to make the biologically important pharmacophore in a single step with facility from readily accessible reagents.

What is claimed is:

1. A method for producing a pyridopyrimidone of the formula

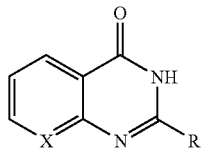

wherein X is N or CH and R is an aryl, heteroaryl or alkyl group, said method comprising the step of:

reacting an acid derivative of the formula:

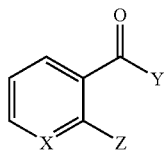

wherein X is N or CH;
Y is an appropriate leaving group;
Z is a halogen, $OR^1$, $NHR^1$, or $SR^1$; and
$R^1$ is a lower alkyl with an amidine derivative of the formula

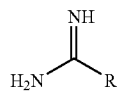

where R is defined as above whereby said pyridopyrimidone is produced.

2. The method of claim 1 wherein Y is $OR^1$, $SR^1$, Cl, F or an activated ester.

3. The method of claim 2 wherein said activated ester is

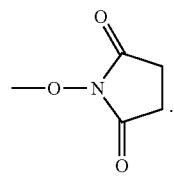

* * * * *